US009726596B2

(12) United States Patent
Dasgupta et al.

(10) Patent No.: US 9,726,596 B2
(45) Date of Patent: Aug. 8, 2017

(54) CONFIGURATIONAL CHIRALITY BASED SEPARATION

(71) Applicant: University of Calcutta, Kolkata, West Bengal (IN)

(72) Inventors: Anjan Kr. Dasgupta, Kolkata (IN); Tamoghna Bhattacharyya, Birbhum (IN); Sarita Roy, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 0 days.

(21) Appl. No.: 14/539,790

(22) Filed: Nov. 12, 2014

(65) Prior Publication Data
US 2015/0131097 A1  May 14, 2015

(30) Foreign Application Priority Data
Nov. 13, 2013  (IN) .......................... 1293/KOL/2013

(51) Int. Cl.
*G01N 21/21*  (2006.01)
*C07D 209/20*  (2006.01)
*G01N 21/19*  (2006.01)
*G01N 21/65*  (2006.01)

(52) U.S. Cl.
CPC ............ *G01N 21/21* (2013.01); *C07D 209/20* (2013.01); *G01N 21/19* (2013.01); *G01N 21/65* (2013.01); *G01N 2021/216* (2013.01)

(58) Field of Classification Search
CPC ..................................................... G01N 21/21
See application file for complete search history.

(56) References Cited

U.S. PATENT DOCUMENTS

| 2002/0137233 A1* | 9/2002 | Stevens | B82Y 10/00 436/531 |
| 2003/0157016 A1* | 8/2003 | Bolskar | B82Y 30/00 423/461 |
| 2004/0120880 A1* | 6/2004 | Zhang | B07C 5/12 423/460 |
| 2004/0147594 A1* | 7/2004 | Setchell | A23L 1/30 514/456 |
| 2008/0217588 A1* | 9/2008 | Arnold | B82Y 30/00 252/502 |

(Continued)

FOREIGN PATENT DOCUMENTS

WO    WO-03/072352 A1    9/2003

OTHER PUBLICATIONS

Chang, Y., et al., "Effect of Single-walled Carbon Nanotubes on Cellulose Phenylcarbamate Chiral Stationary Phases," Chemical Research in Chinese Universities, vol. 23, Issue 6, pp. 646-649 (Nov. 2007).

(Continued)

*Primary Examiner* — Tarifur Chowdhury
*Assistant Examiner* — Omar Nixon
(74) *Attorney, Agent, or Firm* — Maschoff Brennan

(57) ABSTRACT

A method of determining the relative concentrations of enantiomeric forms of a compound in an enantiomeric mixture includes combining the enantiomeric mixture with carbon nanotubes or graphene to form a carbon-enantiomer mixture, exposing the mixture to a monochromatic polarized light, and analyzing reflected polarized light from the mixture using a differential analyzer.

19 Claims, 9 Drawing Sheets

Zigzag SWNT (n,m)
here m=0

Chiral SWNT (n,m)
n≠m≠0

(56) References Cited

U.S. PATENT DOCUMENTS

| | | | | |
|---|---|---|---|---|
| 2009/0246169 | A1* | 10/2009 | Vennemann | C07D 471/14 424/85.2 |
| 2010/0220074 | A1* | 9/2010 | Irvin, Jr. | G06F 3/045 345/174 |
| 2010/0256354 | A1* | 10/2010 | Ishihara | B01D 57/00 540/145 |
| 2011/0201593 | A1* | 8/2011 | Babu | C07D 487/10 514/210.18 |
| 2012/0267551 | A1* | 10/2012 | Dasgupta | G01N 21/6445 250/453.11 |

OTHER PUBLICATIONS

Chiang, W., and Sankaran, R. M., "Linking catalyst composition to chirality distributions of as-grown single-walled carbon nanotubes by tuning $Ni_xFe_{1-x}$ nanoparticles," Nature Materials 8, pp. 882-886 (Sep. 20, 2009).

Chiang, W.-H., et al., "Nanoengineering $Ni_xFe_{1-x}$ Catalysts for Gas-Phase, Selective Synthesis of Semiconducting Single-Walled Carbon Nanotubes," ACS Nano, vol. 3, Issue 12, pp. 4023-4032 (Dec. 2, 2009).

Colomer J. F., et al., "Large-scale synthesis of single-wall carbon nanotubes by catalytic chemical vapor deposition (CCVD) method," Chemical Physics Letters, vol. 317, Issues 1-2, pp. 83-89 (Jan. 28, 2000).

Greenfield, N.J., "Biomacromolecular Applications of Circular Dichroism and ORD," Encyclopedia of Spectroscopy and Spectrometry, pp. 117-130, (1999).

Greenfield, N.J., "Methods to estimate the conformation of proteins and polypeptides from circular dichroism data," Analytical Biochemistry, vol. 235, pp. 1-10 (Mar. 1996).

Iijima, S., "Helical Microtubules of Graphitic Carbon," Nature, vol. 354, pp. 56-58 (Nov. 7, 1991).

Kolmogorov, A.N. and Crespi, V. H., "Nanotube-substrate interactions: Distinguishing carbon nanotubes by the helical angle," Physical Review Letters, vol. 92, No. 8, pp. 085503-1-085503-4 (Feb. 27, 2004).

Moliner-Martínez, Y., et al., "Evaluation of carbon nanostructures as chiral selectors for direct enantiomeric separation of ephedrines by EKC," Electrophoresis, vol. 15, pp. 2573-2579 (Aug. 28, 2007).

Pichler, T., "Viewpoint: Unraveling Electron Chirality in Graphene," American Physical Society, accessed at http://web.archive.org/web/20130528110242/http://physics.aps.org/articles/v4/79, published on Oct. 10, 2011, pp. 4.

Roy, S., et al., "Nanoparticle induced conformational change in DNA and chirality of silver nanoclusters," J Nanosci Nanotechnol, vol. 10, Issue 2, pp. 819-825 (Feb. 2010).

Saito, R., et al., "Electronic structure of chiral grapheme tubules," Appl. Phys. Lett., vol. 60, Issue 18, pp. 2204-2206 (May 4, 1992).

Song, W., et al., "Synthesis of Bandgap-Controlled Semiconducting Single-Walled Carbon Nanotubes," ACS NANO, vol. 4, No. 2, pp. 1012-1018 (Jan. 27, 2010).

Vardanega, D., et al., "Chiral response of single walled carbon nanotube based sensors to adsorption of amino acids: A theoretical model," J. Chem. Phys., vol. 127, Issue 19, pp. 12, (2007).

\* cited by examiner

Zigzag SWNT (n,m)
here m=0

Chiral SWNT (n,m)
n≠m≠0

CONFIGURATIONAL CHIRALITY BASED SEPARATION

CROSS-REFERENCE TO RELATED APPLICATION

The present application claims priority to Indian Patent Application No. 1293/KOL/2013, filed on Nov. 13, 2013, the contents of which are incorporated herein by reference in their entirety.

FIELD

The present technology relates to separation technology, more particularly to configurational chirality based separation technology.

BACKGROUND

The following description is provided to assist the understanding of the reader. None of the information provided or references cited is admitted to be prior art to the present technology.

The carbon atoms in single-wall carbon nanotubes are arranged in long, hollow cylinders. The carbon nanotubes may also exist as multi-walled nanotubes where a series of smaller tubes are contained within a larger outer shell in a nested, concentric arrangement. The angle at which the sheet of carbon atoms rolls into the nanotube imparts a characteristic "twist" to the structure of carbon nanotubes. This twist is known as the "chirality" of the tube. The chirality can be represented by a chiral vector (n, m) that contains information on both the angle of twist and diameter of the tube. The chirality distribution and the band gap of CNTs can be tuned. Theoretical and experimental observations have confirmed that carbon nanotubes will act as metals or as semi-metals when $|n-m|=3q$, where q is an integer value. Otherwise, nanotubes behave as semiconductors, with a band gap which is inversely proportional to their diameter.

Chirality can be geometrical as well as topological. The chirality of single-wall nanotubes (SWNTs) and graphene is primarily topological or configurational. On the other hand, the enantiomeric forms commonly observed in simple organic molecules (e.g., L and D amino acids) assume geometrical chirality. The interaction of these two chiral entities has rarely been studied.

SUMMARY

In one aspect, a method is provided for determining the relative concentrations of enantiomeric forms of a compound in a racemic mixture. The method includes combining the racemic mixture with carbon nanotubes to form a carbon-enantiomer mixture, exposing the mixture to a monochromatic polarized light, and analyzing reflected polarized light from the mixture using a differential analyzer.

In another aspect, a method is provided for determining an enantiomeric form of a chiral compound. The method includes combining the chiral compound with a first concentration of carbon nanotubes to form a first carbon-enantiomer mixture, combining the chiral compound with a second concentration of carbon nanotubes to form a second carbon-enantiomer mixture, combining the chiral compound a third concentration of carbon nanotubes to form a third carbon-enantiomer mixture, determining a fractional ellipticity of the first, second, and third carbon-enantiomer mixtures in a circular dichroism experiment; and plotting the fractional ellipticity values against the first, second, and third concentration values. In the method, a convex plot reveals that the enantiomeric form is levorotatory and a concave plot reveals that the enantiomeric form is dextrorotary.

In another aspect, a method is provided for determining a concentration of zigzag conformation single-walled carbon nanotubes in a solution. The method includes contacting a solution including single-walled carbon nanotubes with a solution including an enantiomerically pure compound to form a mixed solution, measuring the change in ellipticity of the solution as a function of wavelength in a circular dichroism experiment, comparing the change in ellipticity of the solution to a change in ellipticity of standardized concentration solutions of zigzag conformation single-walled carbon nanotubes, and determining the concentration of the zigzag conformation single-walled carbon nanotubes in the solution.

In another aspect, a method for chiral separation is provided. The method includes contacting a first solution with a column, wherein the first solution includes a mixture of a first enantiomer and a second enantiomer, and the column includes single-walled nanotubes, multi-walled nanotubes, or graphene, eluting from the column a second solution comprising an elevated concentration of the first enantiomer as compared to a concentration of the first enantiomer in the first solution.

In another aspect, a method is provided for determining chirality of carbon nanotubes. The method includes contacting a solution of carbon nanotubes with a solution including an enantiomerically pure compound to form a mixed solution, and determining whether the mixed solution exhibits a co-operativity or not by circular dichroism. In the method, if co-operativity is exhibited, it confirms that the carbon nanotube is of a zigzag conformation.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Figure 1:
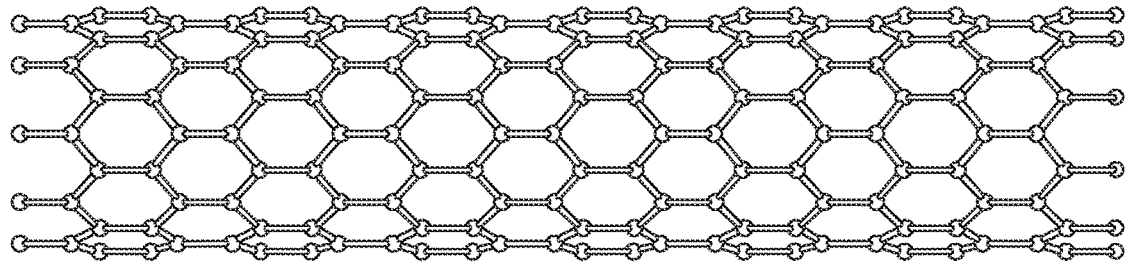
FIG. 1 is a schematic representation of zigzag and chiral single-walled nanotubes.
Figure 1:
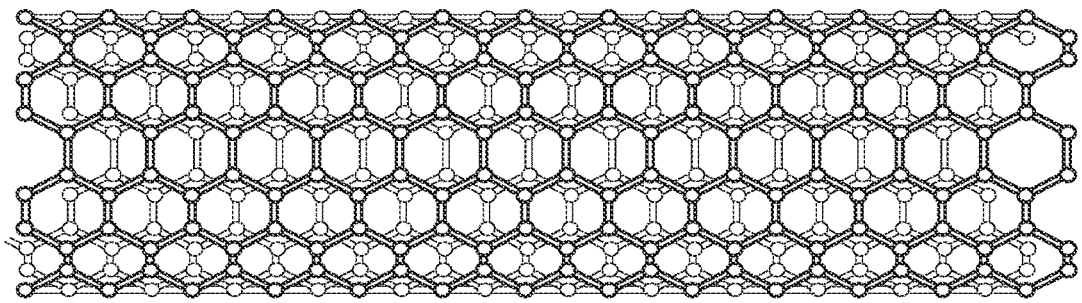

The present technology provides a method for differentiating chiral isomers of a compound from each other using single-walled nanotubes (SWNTs). Pristine, single-wall carbon nanotubes (SWNTs) which may be either metallic or semiconducting, may exist in either a chiral or a zigzag configuration as shown in FIG. 1. The differential affinity of zigzag pristine SWNT is different, for various enantiomeric molecules. The binding profile with levorotatory (L) and dextrorotatory (D) forms changes from a concave pattern to a convex pattern, respectively. Concave patterns are indicative of a positive co-operativity, while convex patterns are indicative of a negative co-operativity. As used herein, co-operativity, refers to the ability of a material to bind to a SWNT. Where the co-operativity is positive, the binding of the first material enhances the binding of additional materials, whereas when the co-operativity is negative, the binding of the first material reduces the binding of additional materials.

The chiral, discriminator-like activity of pristine SWNTs can be exploited as an enantiomeric column material, in determining the chirality of the SWNT or graphene. The binding of the pristine carbon nanotube shows a reciprocal nature of co-operativity in binding two geometric chiral forms (L- and D-tryptophan). This co-operativity may allow the carbon nanotubes as a potential chiral column material. Reciprocally, such chiral column materials may be used to characterize and purify other carbon nanotubes (CNTs), either single-wall or multi-wall, or even graphene, based upon differential binding profiles.

Figure 2:
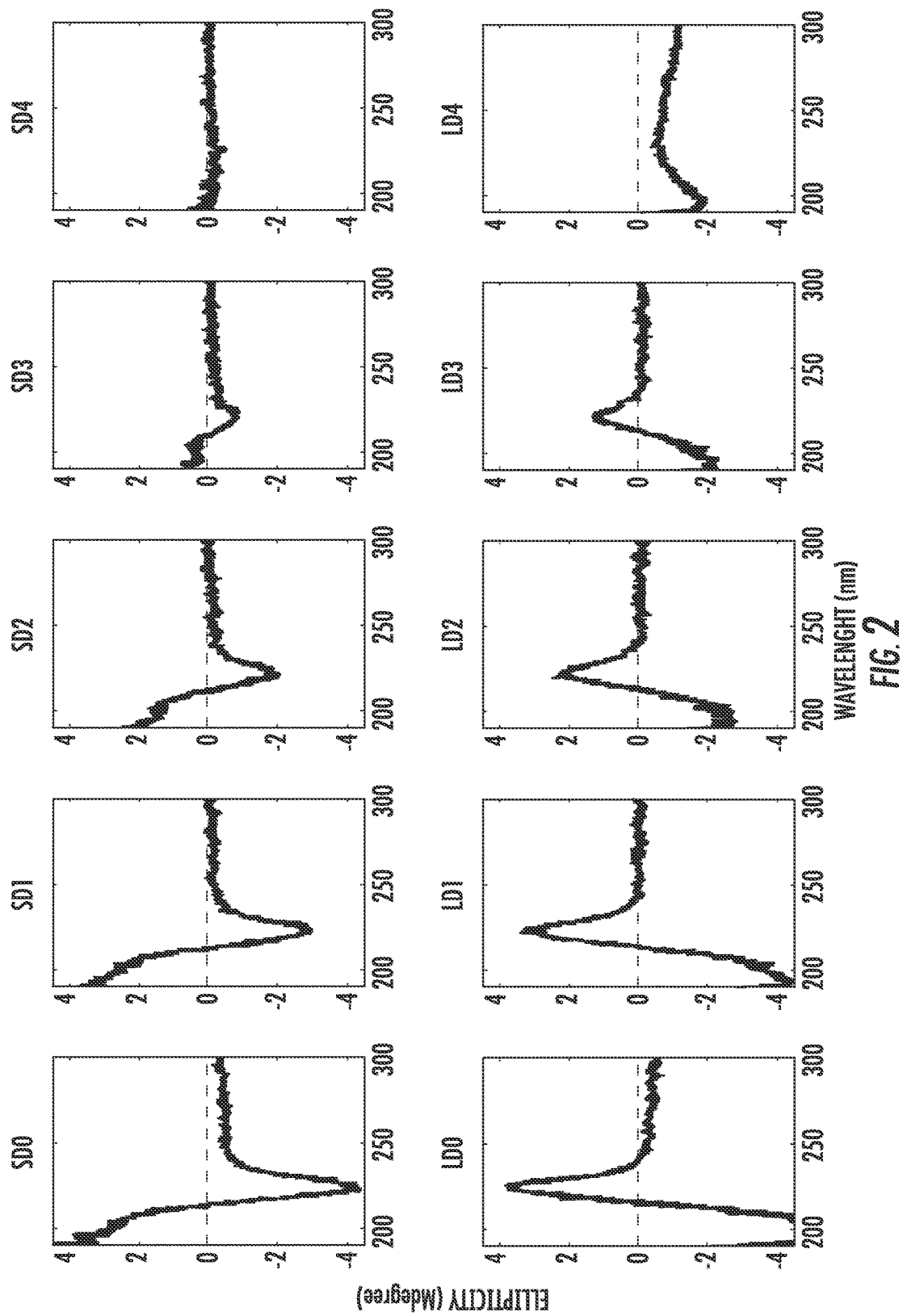
FIG. 2 is a differential circular dichroism (CD) pattern of D-tryptophan and L-tryptophan interacting with different concentrations of single-walled nanotubes, where the "D" and "L" indicate D-tryptophan and L-tryptophan, respectively, and the 0, 1, 2, 3, and 4 indicates the concentration of the single-walled nanotubes at 0, 0.2857, 0.5714, 0.8571, and 1.4286 mg/ml, respectively, according to the examples.

FIG. 2 illustrates that the percent racemization in a racemic mixture can be determined using the differential incremental binding of the enantiomers with nanomaterials. For example, the enantiospecific binding affinity of SWNTs can be applied to the detection of L- and D-chiral forms from a racemic mixture, referring to the circular dichroism spectrum with reference enantiomers. In FIG. 2, mixtures of SWNTs with L- or D-tryptophan were prepared at ratios of 1:4, 2:3, 3:2 and 4:1. From the figure, it is clear that both the L- and D-tryptophan differentially bind with achiral SWNTs. The L-tryptophan provides a stronger signal response (55.47 for 4:1 L/D ratio, 25.79 for 3:2 L/D ratio) than the D-tryptophan response (51.18 for 4:1 D/L ratio, 23.77 for 3:2 D/L ratio), when both are simultaneously present in a racemic mixture. Thus zigzag SWNTs can be used as enantiospecific adsorbents (chiral column) for different chiral molecules such as drugs.

The selectivity of L-tryptophan and D-tryptophan for SWNTs can be enhanced if the configurational chirality of the SWNT is altered. For example, if chiral or armchair SWNTs are used, the adsorption of a particular enantiomer on the surface of the SWNT may be enhanced as compared to the adsorption of the same enantiomer to an achiral SWNT. The terms chiral, armchair, and zigzag refer to the rolling of a graphene sheet to form the SWNT. As is understood in the art, the rolling of the sheet may be described by use of a de Heer abacus where, to realize a (n,m) tube, one moves n times on a vector a1 and m times on a vector a2 from the origin to get to point (n,m). The sheet is then rolled so that the two points coincide. In chiral SWNTs n≠m≠0, in zigzag SWNTs m=0, and in armchair SWNTs n=m. Chiral and zigzag SWNTs are illustrated in FIG. 1.

Reciprocally, carbon nanomaterials with different electrical or electronic properties and complex shapes (such as monolayer or multilayer sheets) may be differentiated using optical methods. For example, using polarization studies with conjugated or surface bound achiral probes, SWNT concentrations or configurations may be differentiated from one another, and may further be separated using flow cytometric methods (i.e. using a program sorter). Chirality sorting by flow cytometric methods may be achieved by using additional polarizers in the scattering detector paths.

In one aspect, a method is provided for determining the relative concentrations of enantiomeric forms of a compound in a racemic mixture. The method includes combining the racemic mixture with carbon nanotubes or graphene to form a carbon-enantiomer mixture, exposing the mixture to a monochromatic polarized light, and analyzing reflected polarized light from the mixture using a differential analyzer. In some embodiments, the analyzing step may include observing a differential binding parameter of the carbon-enantiomer mixture in a circular dichroism experiment; and comparing the differential-binding parameter of the carbon-enantiomer mixture to a known differential-binding parameter curve of known concentration carbon-enantiomer mixtures to determine the relative concentrations of the enantiomeric forms in the racemic mixture. Accordingly, standardization curves may be prepared to determine relative concentrations of the enantiomeric forms of the compound in the racemic mixture. Without being bound by theory, it is believed that the carbon nanotubes or graphene and the enantiomer are coupled via a non-covalent adsorption of the enantiomer to the surface of the carbon nanotubes or graphene.

In the methods, the combining may include sonicating the racemic mixture with the carbon nanotubes or graphene. The sonicating disperses the carbon nanotubes or graphene and racemic mixture in the solution such that both components are solubilized in the solvent of choice. Suitable solvents (i.e. media) include, but are not limited to, water, acetone, toluene, and carbon tetrachloride. In some embodiments, the racemic mixture is sonicated with carbon nanotubes. In other embodiments, the racemic mixture is sonicated with graphene.

In another aspect, a method is provided for determining an enantiomeric form of a chiral compound. The method may include combining the chiral compound with a first concentration of carbon nanotubes to form a first carbon-enantiomer mixture, combining the chiral compound with a second concentration of carbon nanotubes to form a second carbon-enantiomer mixture, combining the chiral compound with a third concentration of carbon nanotubes to form a third carbon-enantiomer mixture. Finally, the method includes determining a fractional ellipticity of the first, second, and third carbon-enantiomer mixtures using circular dichroism, and plotting the fractional ellipticity values against the first, second, and third concentration values. In the method, a convex plot reveals that the enantiomeric form is levorotatory, while a concave plot reveals that the enantiomeric form is dextrorotary. As will be appreciated, the three measurements are used to determine if the resulting plot is a concave plot (that is the line formed is a "U" shaped arc), or a convex plot (that is the lined formed is an "∩" upside-down "U" shaped arc).

In some embodiments, the combining includes sonicating the carbon-enantiomer mixtures. The carbon nanotubes used in the method may be single-walled carbon nanotubes or multi-walled carbon nanotubes. In some embodiments, the carbon nanotubes are single-walled carbon nanotubes having a zigzag conformation.

The interacting step of the method may be conducted in a suitable medium of choice. In some embodiments, the medium includes, but is not limited to, water, acetone, toluene, and carbon tetrachloride.

In the method, different concentrations of the carbon nanotubes are used. The first concentration may be a relatively low concentration, while the second concentration may be higher than the first concentration, whereas the third concentration may be relatively higher than the first and second concentrations. As illustrations of the relative concentrations, and according to some embodiments, the first concentration of carbon nanotubes may be greater than 0 mg/ml and less than or equal to about 0.5 mg/ml, the second concentration may be about 0.5 mg/ml to about 1.0 mg/ml, and the third concentration of carbon nanotubes may be about 1.0 mg/ml to about 1.5 mg/ml. The exact concentration of the carbon nanotubes is not particularly important, but they can be statistically different and far enough apart such that the concave or convex line shapes may be determined.

In some any of the above methods, the chiral (or enantiomeric) compound may be any compound possessing at least one chiral center and for those compounds with more than one chiral center, it may be any such compound as long as it is optically active and not a meso form. This includes many pharmaceutical and non-pharmaceutical compounds. Two such compounds are tryptophan and ibuprofen, however, the enantiomeric compounds should not be so limited, as long as they are optically active isomers that will provide a CD response. Where the compound is tryptophan it may be D-tryptophan or L-tryptophan, and where it is ibuprofen, it may be D-ibuprofen or L-ibuprofen.

In another aspect, a method is provided for determining a concentration of zigzag conformation single-walled carbon nanotubes in a solution. The method may include contacting a solution including single-walled carbon nanotubes with a solution including an enantiomerically pure compound to form a mixed solution, measuring the change in ellipticity of the solution as a function of wavelength using circular dichroism, comparing the change in ellipticity of the solution to a change in ellipticity of standardized concentration solutions of zigzag conformation single-walled carbon nanotubes; and determining the concentration of the zigzag conformation single-walled carbon nanotubes in the solution. In some embodiments, the enantiomerically pure compound is enantiomerically pure tryptophan. For example, it may be enantiomerically pure D-tryptophan, or enantiomerically pure L-tryptophan.

In another aspect, a method is provided for chiral separation. The method includes contacting a first solution with a column, wherein the first solution includes a mixture of a first enantiomer and a second enantiomer, and the column has single-walled nanotubes, multi-walled nanotubes, or graphene; and eluting from the column a second solution including an elevated concentration of the first enantiomer compared to a concentration of the first enantiomer in the first solution. In some embodiments, the first enantiomer is a dextrorotary enantiomer. In other embodiments, the first enantiomer is a levorotatory enantiomer. Accordingly, where the mixture includes a racemic mixture of tryptophan, the first enantiomer may be D-tryptophan and the second enantiomer may be L-tryptophan. Alternatively, where the mixture includes a racemic mixture of tryptophan, the first enantiomer may be L-tryptophan and the second enantiomer may be D-tryptophan.

In the method, the column may be a liquid chromatography column, a high pressure liquid chromatography column, or a flow cytometry column. In the method, the column may include single-walled nanotubes. In the method, the column may include single-walled nanotubes that have a zigzag configuration. In the method, the column may include multi-walled nanotubes. The solutions may include a suitable medium in addition to the chiral compounds. In some embodiments, the suitable medium may be water, acetone, toluene, or carbon tetrachloride.

As noted above, the reciprocal studies may also be conducted, where the chiral compound identifies the carbon nanotube configuration. Accordingly, in another aspect, a method is provided for determining the chirality of carbon nanotubes. Such methods may include contacting a solution of carbon nanotubes with a solution including an enantiomerically pure compound to form a mixed solution, and determining by circular dichroism if the mixed solution exhibits a co-operativity, or no co-operativity. If co-operativity is exhibited the carbon nanotube is of a zigzag conformation.

In some embodiments, the enantiomerically pure compounds may be an enantiomerically pure tryptophan and a co-operativity is exhibited. In other embodiments, the enantiomerically pure tryptophan is D-tryptophan and no co-operativity is exhibited. Conversely, where the enantiomerically pure tryptophan is L-tryptophan, a co-operativity may be exhibited. If co-operativity is exhibited, a degree of co-operativity may be determined and compared a standard co-operativity curve to determine a concentration of the zigzag conformation single-walled carbon nanotubes in the solution of single-walled carbon nanotubes.

The present technology, thus generally described, will be understood more readily by reference to the following Examples, which are provided by way of illustration and are not intended to be limiting of the present technology.

EXAMPLES

Example 1

Preparation of D- and L-Tryptophan Mixtures with SWNTs

Pristine SWNTs were synthesized using published procedures. (Colmer et al. *Chem. Phys. Lett.* 317:83-89 (2000)).

The pristine SWNTs, mixed with water at varying concentrations, according to Table 1, were then sonicated with D- or L-tryptophan (0.2 mM) using a Heilscher US200S Ultrasonic Processor with a 60% amplitude and 0.6 cycles for 8-10 minutes. The mixture of enantiomer and SWNT was then centrifuged. The supernates were collected and observed in a circular dichroism (CD) experiment, the results of which are presented in FIG. 2.

TABLE 1

Sample number and concentration of the SWNT in water.

| Sample No. | Concentration of SWNT. (mg/mL) |
|---|---|
| D-Tryptophan | |
| SD0 | 0 |
| SD1 | 0.2857 |
| SD2 | 0.5714 |
| SD3 | 0.8571 |
| SD4 | 1.4286 |
| L-Tryptophan | |
| SL0 | 0 |
| SL1 | 0.2857 |
| SL2 | 0.5714 |
| SL3 | 0.8571 |
| SL4 | 1.4286 |

Example 2

Raman Spectrum of Pristine SWNTs

Figure 3:
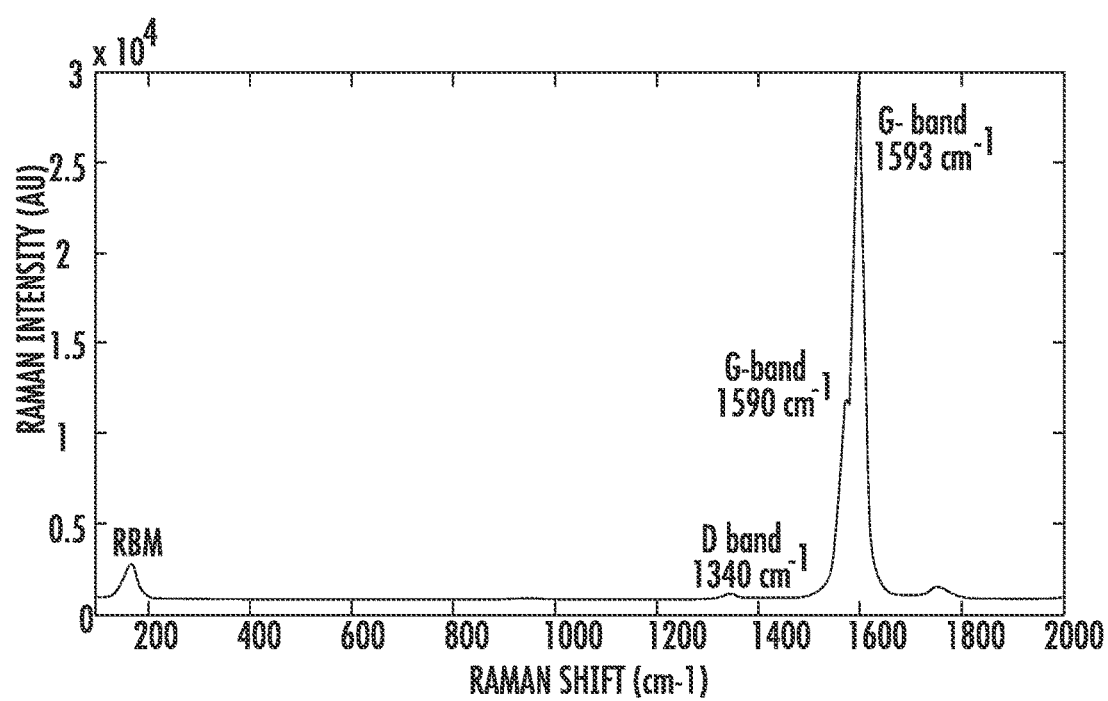
FIG. 3 is a Raman spectrum of pristine single-walled nanotubes, according to the Examples.

Raman spectra of the pristine SWNTs was obtained. A tangential band (G band) was observed at 1593 cm$^{-1}$ (G+ band) and at 1590 cm$^{-1}$ (G− band), while a disorder-induced band (D band) was observed at 1340 cm$^{-1}$ as shown in FIG. 3. The wavenumber of the G band (the Lorentzian fitting curve of G+ and G− bands) confirmed the semiconducting properties of the SWNTs. The minimum intensity of D band confirmed the high purity of the synthesized SWNTs and the single tone modes of the RBMs strengthened the semiconducting properties of the SWNTs.

The measurement of the metallic character of the SWNTs is indicative of their conformation. For example, if the measurement showed them to be metallic, an armchair conformation is present. If the measurement showed them to be semiconducting, a zigzag or chiral conformation is present. However, the two semiconducting conformation may be differentiated by use of CD spectra, where the CD spectra is null, it is zigzag, and where the CD spectra exhibits a signal it is chiral.

Example 3

CD Spectrum of D- and L-Tryptophan—SWNT Mixtures

Figure 4:
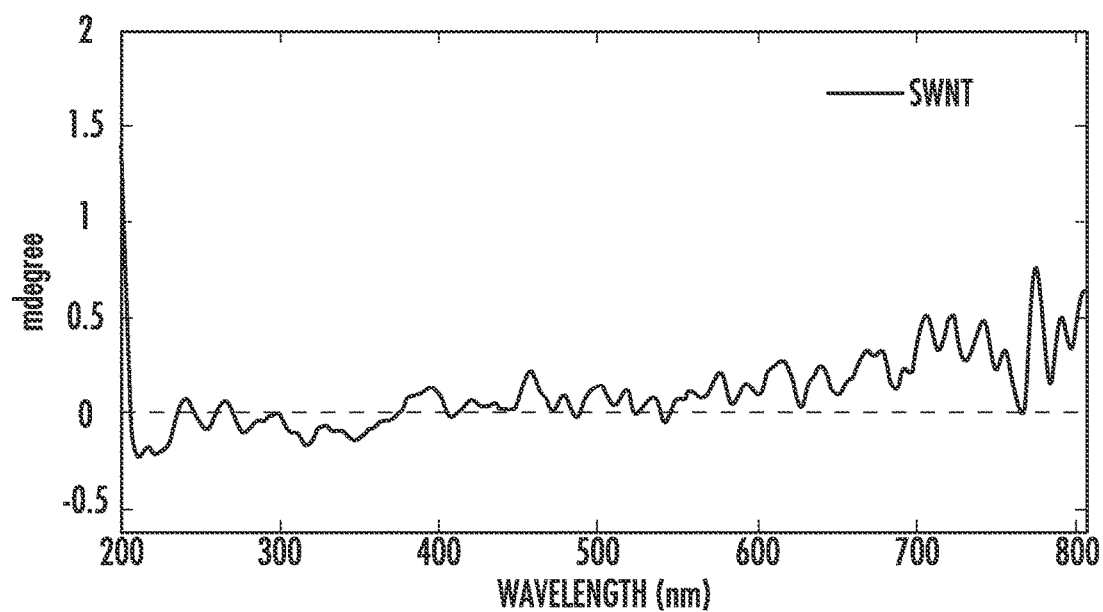
FIG. 4 is a circular dichroism (CD) spectrum of pristine single-walled nanotubes, according to the examples.

As a control, the CD spectrum of the pristine SWNTs was obtained, without observance of a signal as shown in FIG. 4. In contrast, the CD spectrum (see FIG. 2) of enantiomerically pure tryptophan-SWNTs clearly show negative (D-tryptophan) and positive (L-tryptophan) variances under CD measurement. The spectrum of the SWNTs confirms that they have a zigzag structure.

Figure 5A:
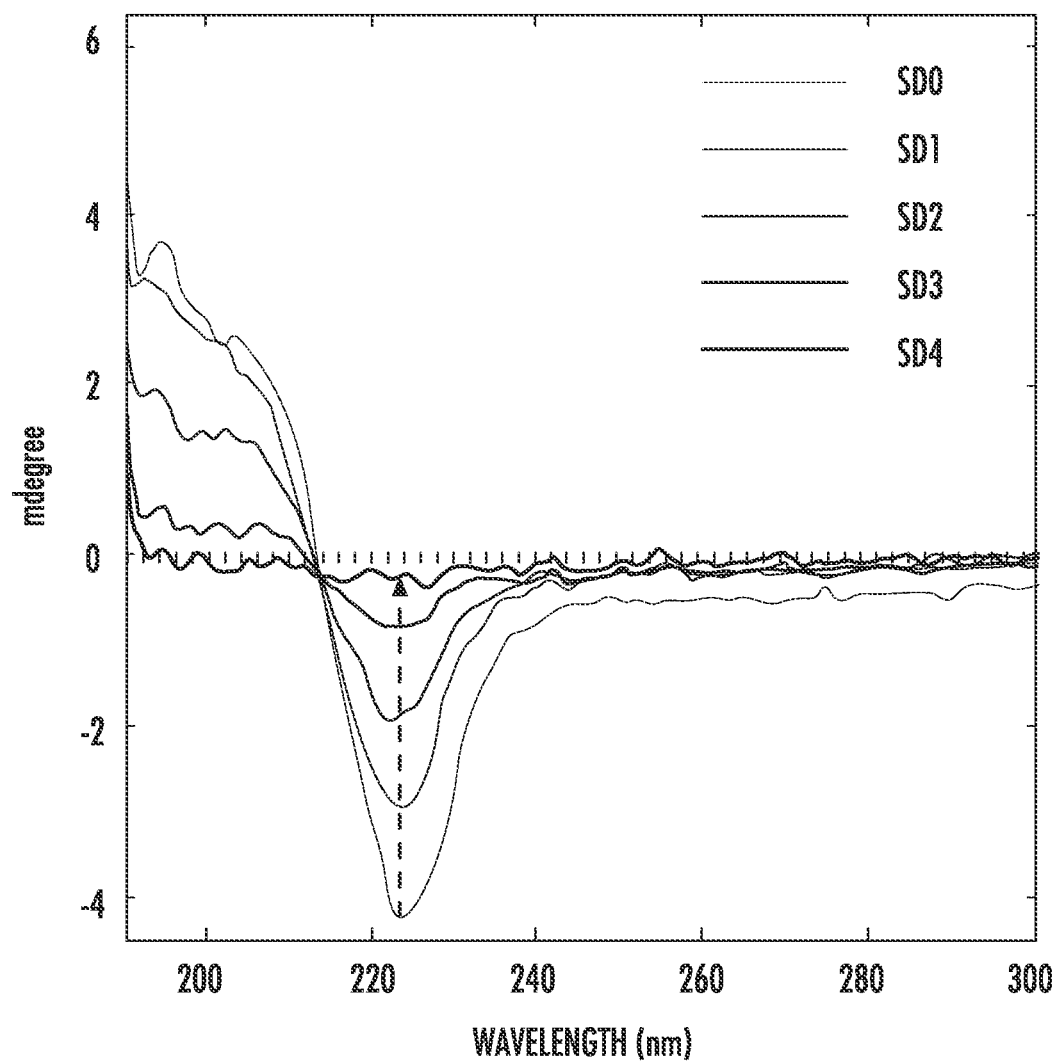
FIGS. 5A and 5B are graphical representations of the change in ellipticity (mdegree) of the interaction between D-tryptophan and single-walled nanotubes and L-tryptophan and single-walled nanotubes, respectively, according to the examples.
Figure 5B:
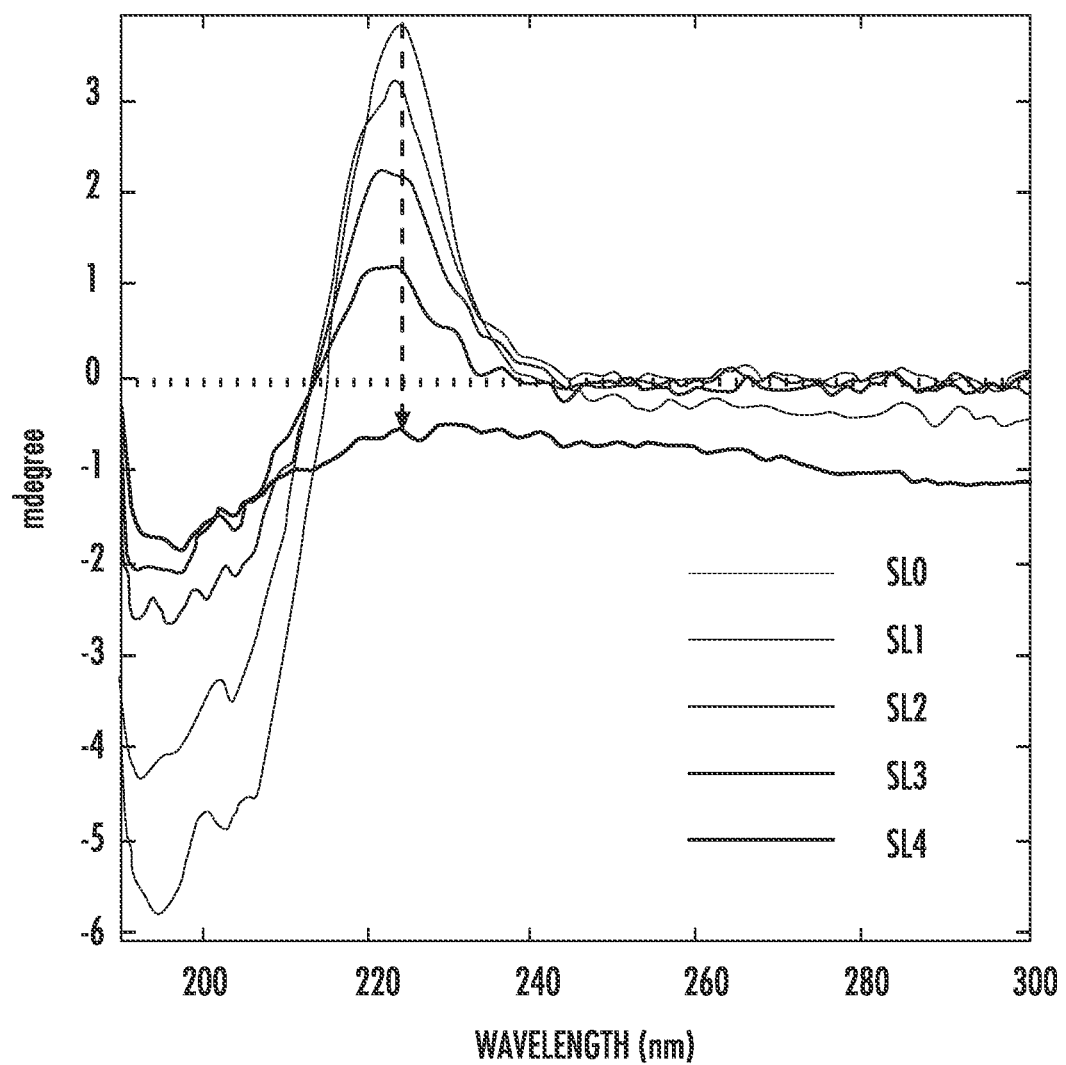

FIGS. 5A and 5B (separately, the FIGS. are overlays of each of the D-tryptophan spectra in FIG. 2 and the L-tryptophan spectra), provide evidence of the interaction of enantiomeric forms of D- (FIG. 5A) and L-tryptophan (FIG. 5B) with increasing concentrations of SWNTs. Amino acids absorb near 220 nm due to the n-π* transition, which occurs due to NH—C=O stretching. In addition to NH—C=O bond, the n-π* transition also occurs in the benzene ring of the tryptophan molecule and hence the strong CD band near 220 nm results. FIGS. 5A and 5B reveal that the mode of interaction of SWNTs is different for D-Trp and L-Trp. The change in ellipticity (mdegree) is greater in the case of L-tryptophan (FIG. 5B) compared to D-tryptophan (FIG. 5A).

Figure 6:
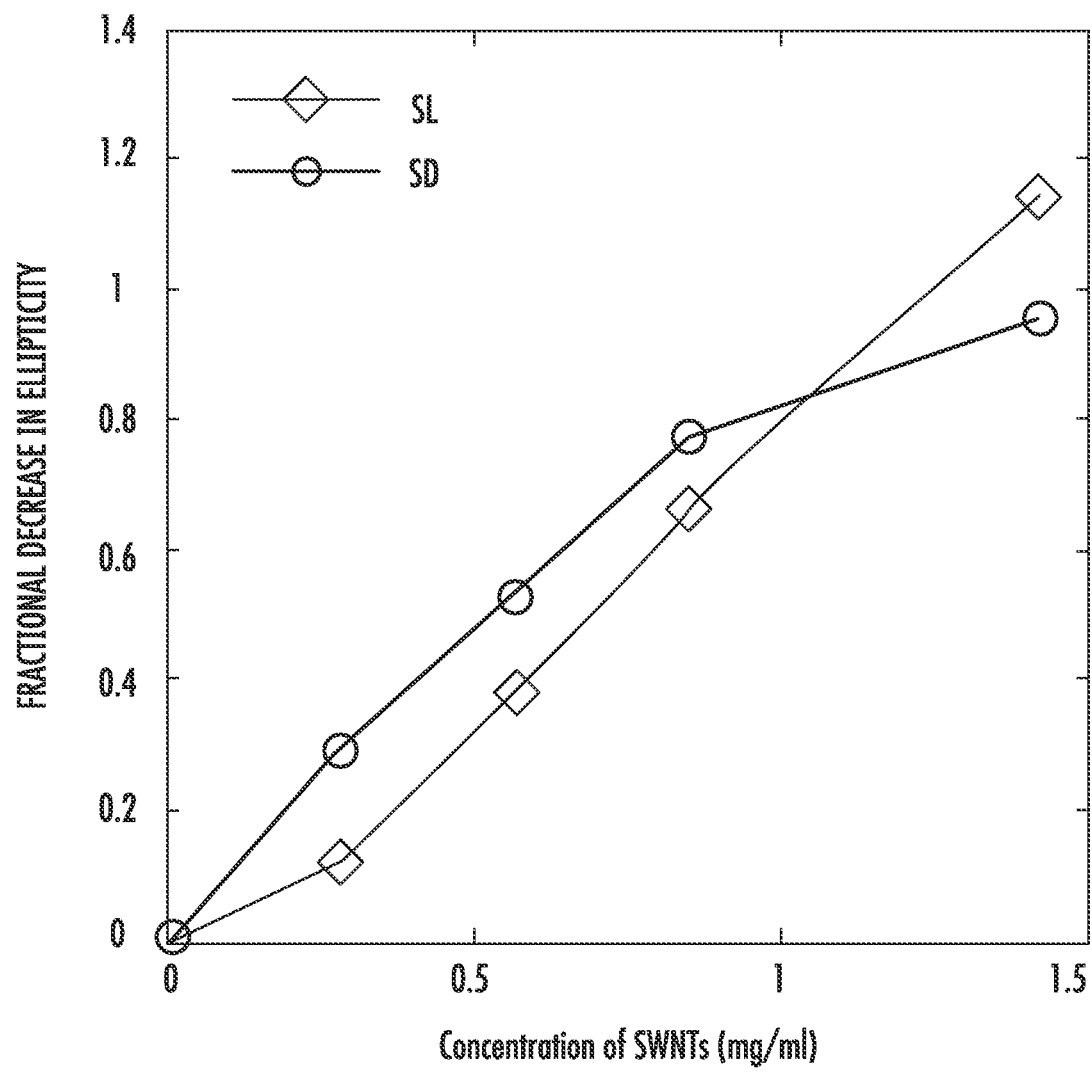
FIG. 6 is a spectral analysis of the CD spectra illustrating the binding nature of SWNTs with D-tryptophan and L-tryptophan and the positive and negative co-operativity as described in the examples.

FIG. 6 is a spectral analysis of the CD spectra illustrating the binding nature of SWNTs with D-tryptophan and L-tryptophan. FIG. 6 illustrates that the binding nature of SWNTs with D-tryptophan shows negative co-operativity while L-tryptophan favors the binding by positive co-operativity. The co-operativity response provides insight into the chiral selection of pristine SWNTs.

This unique chiral selection of pristine SWNTs for identification of enantiomers of amino acids may be generalized for structural identification and discrimination of proteins or enzymes having a unique chiral structure. This may provide a manner in which to predict the three dimensional structures of proteins. Other chemical agents, such as, but not limited to, odor molecules and toxicants like polycyclic aromatic hydrocarbons (PAHs) with differential chiral signatures may be identified and discriminated separately without chemical modification. The process is scalable as the requirement of chiral column material is not necessarily related to the scale of separation. Large scale separation may be effected by increased flow rates.

SWNT-based chiral columns can be used in manufacturing and quality control of drugs where enantiomeric purity may be an important attribute of the activity of the drug, while an undesirable enantiomeric form may often be toxic. Small organic molecules may need detailed and careful enantiomeric screening, and, in this respect, the SWNT-based approach may be useful. Further, because the SWMT columns are generally nonreactive, it may allow for the full recovery of any column-adhered materials. The reciprocal scenario, namely using a standard chiral molecule to classify different chiral forms of SWNT or graphene, can also be performed. This two-way classifier strengthens the potential of the method in drug industries, chemical industries and in carbon nanotube or graphene-based industries.

Example 4

SWNTs Mixed with a Racemic Mixture of L- and D-Tryptophan

Figure 7:
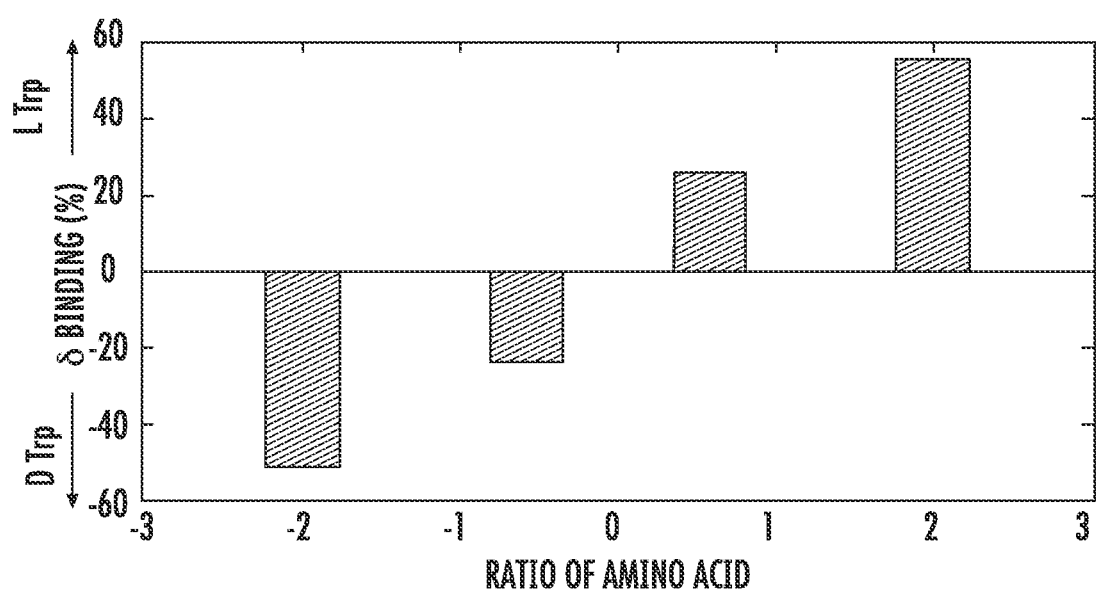
FIG. 7 is a graph of the relative percentage binding of SWNTs with L- and D-tryptophan present in ratios of SWNT:tryptophan of 1:4, 2:3, 3:2 and 4:1, according to the examples.

Of the four samples, they contained 4L:1D, 3L:2D, 3D:2L, and 4L:1D, the L-tryptophan presented a positive δ-binding %, while the D-tryptophan presented a negative δ-binding %. From the FIG. 7 it is clear that both the L- and D-tryptophan differentially bind with zigzag, achiral SWNTs. Interestingly, the L-tryptophan δ-binding % (55.47 for 4:1 L/D ratio and a 25.79 for 3:2 L/D ratio) is a stronger signal response than the D-tryptophan (51.18 for 4:1 D/L ratio, 23.77 for 3:2 D/L ratio). Because of this difference in δ-binding % it is apparent that zigzag SWNTs can be used as enantiospecific adsorbents (chiral column) of different chiral molecules such as drugs. FIG. 7 illustrates that the percent racemization in a racemic mixture can be discriminated using the differential incremental binding of the enantiomers with nanomaterials. For example, the enantiospecific binding affinity of SWNTs can be applied to the detection of L- and D-chiral forms from a racemic mixture, based upon referencing of the circular dichroism spectrum with reference enantiomers.

Example 5

Carbon Nanomaterials with Different Electrical or Electronic Properties and Complexity of Shape (i.e. Monolayer or Multilayer Sheets) can Also be Differentiated by Polarization Studies Using Achiral Probes The chirality based sorting in a flow cytometric platform can be achieved additional using polarizers in the scattering detector paths. In a contour plot, the SSC Pol (side scattering polarization) and SSC Depol (side scattering depolarization) may be placed on the abscissa and the ordinate, respectively. Side scattering are then seen at 0° and 90° polarization angles. In a Raman active mode, an incident electric field produces a dipole by polarizing the electron cloud of each atom. If this induced dipole is modulated by a lattice vibrational mode which depend on Brillion zones (determines the metallic or semiconducting properties) of each nanotube, then a coupling occurs between the incident light and the phonon result inelastic scattering. Thus, the transition dipole moment varies from material to material due to different lattice vibrational modes and the nature of coupling between incident the electric dipole and phonons. The perpendicular scatter collected at 90° (depolarization) is high may be due to complexity on structure. SWNTs are monolayer graphene sheets which are annealed at a high temperature but MWNTs are concentric cylinders of single wall carbon nanotubes/graphene sheets form upon annealing. The torsion angle of each and every cylinder may not be the same or the inter-atomic distances between two sheets may also differ as well. Therefore MWNTs may give rise different mode of coupling result differential response in scattering in comparison with SWNTs and graphene.

Figure 8:
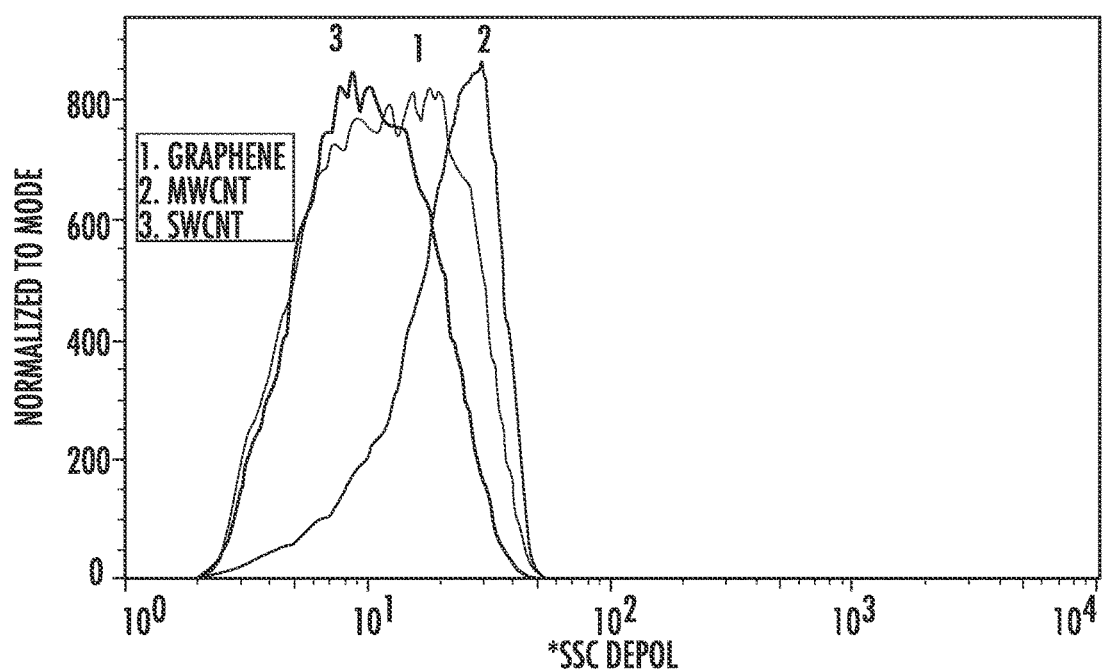
FIG. 8 is a histogram plot of side scatter depolarization (SSC Depol) vs. side scatter polarization (SSC Pol) of tryptophan functionalized SWNTs, MWNTs, and Graphene, according to the examples.

FIG. 8 shows the differentiation of functionalized SWNTs, MWNTs, and graphene. As used herein, "functionalized" is used in a non-traditional sense in that it refers to an adsorptive interaction between the carbon nanotubes and the chiral compounds by other than a covalent bond. In FIG. 8, the side scatter polarization (SSC Pol) as abscissa vs. side scatter depolarization (SSC Depol) as ordinate clearly indicates that SWNTs differ from MWNTs. Interestingly, the data also illustrates that SWNTs and graphenes are similar with respect to side scatter polarization. The scatter signals collected over wide angles can be used to discriminate between different materials. When scatter signals are integrated over wide ranges of such azimuthal angles, the peaks and valleys in the angular distributions tend to cancel each other but other peaks emerge that are characteristic for a given material.

Thus, the chirality of the substrate (SWNT, MWNT, or graphene) can be exploited to separate the materials. In this case, an achiral nanosurface conjugation (SDS) is used to separate the nano-forms which have their intrinsic chirality. We can enhance the resolution of the nano-based separation by choosing chiral conjugants. For example, enantiomerically pure materials, such as, but not limited to, L-tryptophan and D-tryptophan may be used as the chiral conjugant. In that case the differential patterns will be selective to a desired nanomaterial.

Example 6

Preparation of D- and L-Ibuprofen Mixtures with SWNTs

Pristine SWNTs at varying concentrations, according to Table 2, are to be sonicated in water with D- or L-Ibuprofen (0.2 mM) for 8-10 minutes. The mixture of enantiomer and SWNT will then be centrifuged. The supernates are to be collected and observed in a circular dichroism (CD) experiment. It is expected that results similar to those for D- and L-tryptophan will be observed.

TABLE 2

Sample number and concentration of the SWNT in water with D- or L-Ibuprofen.

| Sample No. | Concentration of SWNT. (mg/mL) |
|---|---|
| D- Ibuprofen | |
| 5 | 0 |
| 6 | 0.2857 |
| 7 | 0.5714 |
| 8 | 0.8571 |
| 9 | 1.4286 |
| L- Ibuprofen | |
| 10 | 0 |
| 11 | 0.2857 |
| 12 | 0.5714 |
| 13 | 0.8571 |
| 14 | 1.4286 |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

Other embodiments are set forth in the following claims.

What is claimed is:

1. A method of determining the relative concentrations of each of two enantiomeric forms of a compound in an enantiomeric mixture, the method comprising:
   combining the enantiomeric mixture with carbon nanotubes or graphene to form a carbon-enantiomer mixture;
   exposing the carbon-enantiomer mixture to a monochromatic polarized light;
   analyzing reflected monochromatic polarized light from the carbon-enantiomer mixture using a differential analyzer; and
   determining the relative concentrations of each of the two enantiomeric forms of the compound in the enantiomeric mixture.

2. The method of claim 1, wherein the analyzing step comprises:
   observing a differential binding parameter of the carbon-enantiomer mixture in a circular dichroism experiment; and
   comparing the differential-binding parameter of the carbon-enantiomer mixture to a known differential-binding parameter curve of known concentration carbon-enantiomer mixtures to determine the relative concentrations of the enantiomeric forms in the enantiomeric mixture.

3. The method of claim 1, wherein the combining comprises sonicating the enantiomeric mixture with the carbon nanotubes or the graphene.

4. The method of claim 3, wherein the enantiomeric mixture is sonicated with the carbon nanotubes.

5. The method of claim 4, wherein the carbon nanotubes are in a zigzag conformation.

6. The method of claim 3, wherein the enantiomeric mixture is sonicated with the graphene.

7. The method of claim 3, wherein the enantiomeric mixture and the carbon nanotubes or the graphene are combined in water.

8. The method of claim 1, wherein the method comprises combining the enantiomeric mixture with the graphene to form the carbon-enantiomer mixture.

9. The method of claim 8, wherein the combining comprises sonicating the enantiomeric mixture with the graphene.

10. A method of determining a concentration of zigzag conformation single-walled carbon nanotubes in a solution, the method comprising:
    contacting the solution comprising single-walled carbon nanotubes with a solution comprising an enantiomerically pure compound to form a mixed solution;
    measuring a change in ellipticity of the solution as a function of wavelength in a circular dichroism experiment;
    comparing the change in ellipticity of the solution to a change in ellipticity of standardized concentration solutions of the zigzag conformation single-walled carbon nanotubes; and
    determining the concentration of the zigzag conformation single-walled carbon nanotubes in the solution.

11. The method of claim 10, wherein the enantiomerically pure compound is enantiomerically pure tryptophan.

12. A method of chiral separation comprising:
    contacting a first solution with a column, wherein the first solution comprises a mixture of a first enantiomer and a second enantiomer, and the column consists essentially of single-walled carbon nanotubes, multi-walled carbon nanotubes, or graphene;
    eluting from the column a second solution comprising an elevated concentration of the first enantiomer as compared to a concentration of the first enantiomer in the first solution.

13. The method of claim 12, wherein the first enantiomer is a dextrorotary enantiomer.

14. The method of claim 12, wherein the first enantiomer is a levorotatory enantiomer.

15. The method of claim 12, wherein the first enantiomer is D-tryptophan and the second enantiomer is L-tryptophan.

16. The method of claim 12, wherein the column is a liquid chromatography column, a high pressure liquid chromatography column, or a flow cytometry column.

17. The method of claim 12, wherein the column comprises single-walled carbon nanotubes.

18. The method of claim 17, wherein the single-walled carbon nanotubes have a zigzag configuration.

19. The method of claim 12, wherein the first solution and the second solution comprise water, acetone, toluene, and carbon tetrachloride.

* * * * *